June 11, 1963 C. H. FISCHER Plant Pat. 2,264
GLADIOLUS PLANT
Filed June 28, 1962
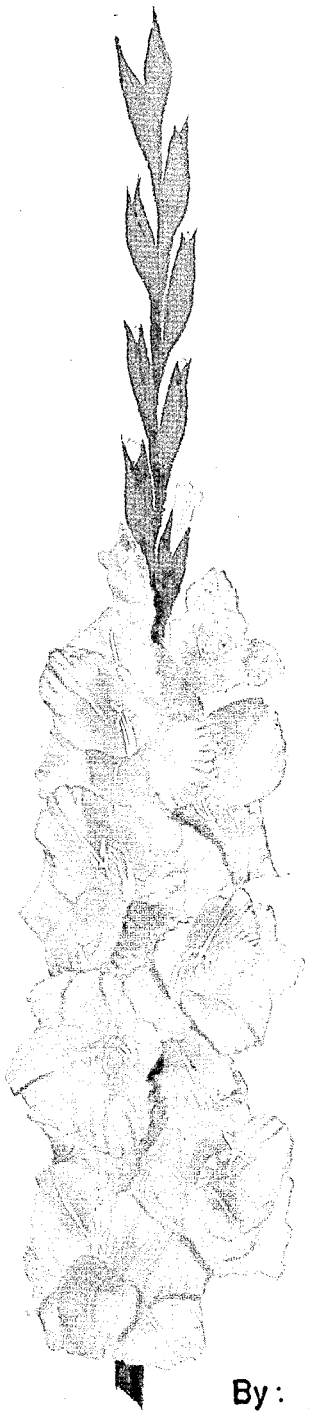
INVENTOR
Carl H. Fischer
By: Lamont Johnston
ATTORNEY United States Patent Office Plant Pat. 2,264
Patented June 11, 1963

2,264
GLADIOLUS PLANT

Carl H. Fischer, St. Charles, Minn., assignor to Selected Glads, Inc., New Albany, Ind., a corporation of Tennessee Filed June 28, 1962, Ser. No. 206,112
1 Claim. (Cl. Plt.—85)

My present invention relates to a new and unusual variety of gladiolus plant and is notable particularly for its brilliant coloring, broad flowerhead, height and, clean, round, disease-free bulbs. I have identified this new variety as seedling #2004–54 in my breeding work.

To the best of my knowledge, this new variety is the result of a cross between the varieties Fire Gleam and Red Wing (both unpatented). Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proven to be permanently fixed.

The illustration, made a part of this application, shows a single bloom spike of this variety, reduced in size, and is as nearly true to color as it is possible to depict. The illustration shows the bright coloring and double-row placement of the florets.

In the following detailed description, color plate references are to the "Horticultural Colour Chart," by The British Colour Council. Where there are other references to color, the ordinary dictionary meanings of the terms are intended.

*The Plant*

Growth: Extremely vigorous. Bloom spike averages 60 to 64 inches in height over-all. Average propagator.

Blooming: The variety is a mid-season bloomer, coming into bloom in 85 to 90 days in the North from large bulbs.

Stems: Straight and willowy. Diameter at base of cutting stem is ⅝ inch. Stem is Magnolia Purple $o30/_1$.

Foliage: Healthy, deep blue-green; leaves are broad, upright, fan-shaped. Leaves are 2 inches wide. Plant foliage, excluding the flower spike, is 36 to 40 inches tall. Disease resistance: This variety has been found unusually resistant to Fusarium yellows, Sclerotina dry rot and Septoria leaf spot, to which some other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases whereas this variety remained healthy and unaffected.

Corms: Unusually round and smooth; high-crowned. Husk covers corm very well; has a purplish color. Flesh is Spanish Orange $o10/_1$ to $o10/_2$.

*The Flower*

Spike: Flowerhead is 24 to 30 inches long with eighteen to twenty-two buds of which six to eight open at one time and six to eight show color.

Bud:

*Size.*—Opening bud is 3¼ inches long.

*Opening.*—Six to eight will show color at one time.

Flower:

*Arrangement.*—The florets are formally placed in a double row on the stem.

*Size.*—Individual florets are large, measuring 5 to 5½ inches in diameter. Upper blooms are progressively smaller.

*Form.*—The florets are round and broad; wide open, slightly ruffled and somewhat recurved.

*Keeping qualities.*—Keeps and opens quite well for a glad in this color. Reds are usually poor openers.

Petals:

*Shape.*—Petals are broad, slightly ruffled and recurved.

*Size.*—The outer petals are 2½ inches across; inner petals 1¾ inches across.

*Aspect.*—Substance is average. Surface is smooth; frilled at edges.

*Fragrance.*—None.

*Color.*—General effect is Dutch Vermilion, $717/_2$, $717/_1$ at the edges shading to $717/_3$ toward the throat. Blotch is $717/_1$. A cream line in throat is bordered with faint China Rose o24. Mid-ribs are faint cream.

Reproductive organs:

*Stamens.*—Cream.

*Pistil.*—Tint of Dutch Vermilion $717/_3$.

*Comparisons*

My new variety resembles Red Wing (unpatented) more than any other variety, but differs from it principally as follows:

(1) My variety is taller.
(2) My variety has healthier, cleaner, rounder bulbs.
(3) My variety has larger florets.
(4) My variety is more disease resistant.

Having thus disclosed my invention, I claim:

The new and distinct variety of gladiolus plant, substantially as herein shown and described, characterized by its brilliant coloring, broad flowerhead and excellent height.

No reference cited.